United States Patent [19]

Sawa

[11] 4,266,861
[45] May 12, 1981

[54] EYE FUNDUS CAMERA

[75] Inventor: Seiji Sawa, Sakai, Japan

[73] Assignee: Minolta Camera Kabushiki Kaisha, Osaka, Japan

[21] Appl. No.: 959,079

[22] Filed: Nov. 9, 1978

[30] Foreign Application Priority Data

Nov. 15, 1977 [JP] Japan ............... 52-137695

[51] Int. Cl.³ ............... A61B 3/10; A61B 3/14; G03B 29/00
[52] U.S. Cl. ............... 351/7; 351/16; 354/62
[58] Field of Search ............... 351/7, 13, 16, 6, 14; 354/62; 350/166

[56] References Cited

U.S. PATENT DOCUMENTS

| | | | |
|---|---|---|---|
| 3,016,000 | 1/1962 | Noyori | 354/62 |
| 3,925,793 | 12/1975 | Matsumura et al. | 354/62 |
| 3,936,844 | 2/1976 | Matsumura | 354/62 |
| 4,068,932 | 1/1978 | Ohta et al. | 351/7 |

FOREIGN PATENT DOCUMENTS 1127947 12/1956 France ............... 351/7

Primary Examiner—John K. Corbin
Assistant Examiner—Rodney B. Bovernick
Attorney, Agent, or Firm—Jackson, Jones & Price

[57] ABSTRACT

An improved eye fundus camera for photographing the fundus of a patient's eye is disclosed. Three separate energy sources are provided which include a first source of a visible light wave length for illuminating the fundus during photography, a second source including at least a first infrared wavelength band for illuminating the cornea of the patient's eye for alignment of the pupil on the optical axis, and a third source including at least a second infrared wavelength band for illuminating the fundus of the patient's eye for focusing the camera on the fundus. A wavelength selective filter is provided on the optical axis having a predetermined aperature. At least one of the infrared light source wavelengths can be transmitted through the filter to provide a full image of the cornea of the patient's eye for alignment purposes.

13 Claims, 3 Drawing Figures

EYE FUNDUS CAMERA

BACKGROUND OF THE INVENTION

1. Field of the Invention

The present invention discloses an improvement in an eye fundus camera and more particularly an improved illumination optical system for aligning the pupil of the eye with the eye fundus camera.

2. Description of the Prior Art

Eye fundus cameras are known in the ophthalogical field for permitting diagnosis of the condition of a patient. A recurrent problem in the use of these instruments comprises the alignment of the center line of the patient's pupil with a photographic optical axis prior to any photography. Generally, this alignment procedure is accomplished by a naked eye monitoring of the front of the eye from a position outside of the photographic optical path.

When working with a non-mydriasis eye fundus camera, no visible light is employed during the prephotographing procedures, and accordingly, alignment cannot be made, simply by the use of the naked eye. It has been suggested in a non-mydriasis fundus camera to use an infrared fundus monitoring system for focus setting. Problems, however, still exist with respect to a precise alignment of a pupil on a photographic axis in a relatively simple procedure.

The following U.S. patents are cited of general interest to disclose various eye fundus cameras that have sought to provide alignment of the pupil with the photographic optical axis, U.S. Pat. No. 4,068,932, U.S. Pat. No. 3,936,844 and U.S. Pat. No. 3,925,793.

The prior art is still seeking a relatively uncomplicated and positive method of aligning the pupil of the eye in an eye fundus camera.

SUMMARY OF THE INVENTION

The present invention provides an improved eye fundus camera employing three separate energy sources for illumination of the patient's eye. A first source provides a visible light wavelength for illuminating the fundus for photography. A second source provides a first infrared wavelength band for illuminating the cornea of the patient's eye for alignment of the pupil on the optical axis, and a third source includes at least a second infrared wavelength band for illuminating the fundus of the patient's eye for focusing the camera on the fundus.

An optical lens system defines an optical path for selective direction of the energy into and from the object eye for both focusing and picture taking, and includes an aperatured wavelength sensitive filter. This filter is capable of reflecting certain wavelengths and selectively transmitting others, whereby a selected infrared wavelength band can be fully transmitted through the filter and thereby permit a full image of the cornea to be utilized for alignment with the pupil of the eye.

The features of the present invention which are believed to be novel are set forth in particularity in the appended claims. The present invention, both as to its organization and manner of operation, together with further objects and advantages thereof, may be best understood by reference to the following description taken in conjunction with the accompanying drawings.

DESCRIPTION OF THE PREFERRED EMBODIMENT

Figure 1:
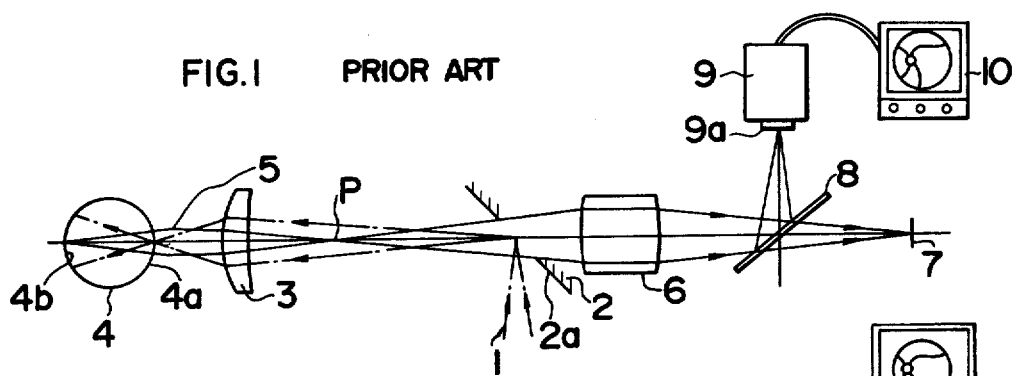
FIG. 1 represents a schematic partial cross-sectional view of a prior art eye fundus camera.

The following specification, taken in conjunction with the drawing, sets forth the preferred embodiment of the present invention in such a manner that any person skilled in the medical and optical field can use the invention. The embodiment of the invention disclosed herein is the best mode contemplated by the inventor for carrying out his invention in a commercial environment, although it should be understood that various modifications can be accomplished within the parameters of the present invention.

This invention will hereinafter be described in detail, reference being had to the accompanying drawings. FIG. 1 is a schematic partial sectional view of a prior art eye fundus camera. The operation of the camera in a photographing procedure is as follows. The photographing light from an electronic flash tube, or the like (not shown), indicated by the chain lines at 1 are reflected by an apertured mirror 2 provided with a central circular aperture. The reflected light is directed thereby towards an objective lens 3. The chain lines 1 indicate only the axial pencil rays simply to show the image forming relationship. Actually, since the portion of the mirror 2 which aligns with the axial pencil rays has been apertured, the light designated by the chain lines do not pass to the objective lens 3, but only the light actually reflected by the peripheral area 2a around the mirror aperture is transmitted to the objective lens 3. As indicated by the chain lines 1, the apertured mirror 2 is located at or near a position conjugate with the front 4a of the eye 4, which is the cornea of the eye, with respect to the objective lens. Therefore, the image of the aperture which is formed by the photographing light 1 reflected on the periphery 2a of the aperture is focused on the front portion 4a of the eye. Since the photographing light 1 reflected on the periphery 2a of the aperture must reach the fundus 4b only through the pupil, the image of the aperture must be smaller in diameter than the pupil. The aperture of the mirror 2 is accordingly dimensioned to satisfy the above condition. The photographing light 1 which enters the interior of the eye in the above manner uniformly illuminates the fundus 4b of the eye. The image of the illuminated fundus 4b is focused at point P by the optical system of the eye and the objective lens. The solid line ray trace 5 indicates the image forming relation of the reflected light from the eye fundus. The image formed at point P is projected through the aperature of the mirror 2 and refocused on a film plane 7 by a relay lens 6 via a half-mirror 8. Since the apertured mirror 2 is located at a distance from position P, the image at point P can be refocused on the film plane 7 by the relay lens 6, without any interference, by the mirror 2.

A portion of the photographing light 1 focused on the eye front 4a does not enter the interior of the eye, but is directly reflected by the cornea. However, the eye front 4a is at or near a position conjugate with the apertured mirror 2 with respect to the objective lens 3 and accordingly the light directly reflected from the eye front 4a returns to the peripheral area 2a of the mirror, thus virtually no reflected light will pass through the aperature. The prior art apertured mirror discharges an important function of causing the photographing light to be incident on the eye while satisfying the condition that it also prevents any undesirable directly reflected light from the eye front 4a from passing into the relay lens, thus only the reflected light from the eye fundus, which is necessary for photographing, will be transmitted to the relay lens.

In monitoring the eye fundus for focusing the photographic optics on the fundus prior to photographing, the following operation is carried out. An infrared illuminating light is caused to be incident on the eye fundus 4b after being reflected at the apertured mirror 2 along the same optical path as that for photographing light 1. Only the reflected light from the eye fundus is selectively refocused on a light-receiving surface 9a of an infrared-responsive TV camera 9 in a monitoring unit by means of the relay lens and a half-mirror 8 in the optical path indicated by the solid line ray trace 5. The light-receiving surface 9a is symmetrical and optically equivalent to the film plane 7 with respect to the half-mirror 8. The video signal from the infrared-responsive TV camera 9 is displayed on a television screen 10 of the monitoring unit for focusing purposes.

The above-described prior art eye fundus camera is not capable of monitoring the front of the eye by means of the monitoring unit 9, 10. As is apparent from the foregoing description, the image of the eye front 4a is formed at the apertured mirror 2. However, the aperture of the apertured mirror 2 has a size corresponding to a part of the image of the eye front 4a which is smaller than the pupil and only the image of this part is allowed to pass through the aperture toward the relay lens. That is to say, a major part of the image of the eye front 4a is projected on the mirror surface of the apertured mirror 2 and, thus, cut off.

For the purpose of aligning the axis of the photographic optics with the center of the pupil, it is necessary that the image of the eye front be monitored over a comparatively broad range including the pupil, but this is not possible with the above-described construction of the apertured mirror 2 which cuts off the directly reflected light from the eye front. Therefore, in order to cut off the directly reflected light from the eye front at the time of photographing and also monitor the whole front of the eye by means of the monitoring unit 9, 10 in the aligning operation, it has been necessary to use relatively complicated construction; for example, it has been suggested that the objective lens 3 be made selectively adjustable for two dissimilar focal lengths with the aid of an auxiliary lens so that the focal length of the objective lens 3 is reduced during aligning purposes to thereby shift the image of the eye front from the position of the apertured mirror 2 to a position closer to the objective lens, e.g., point P.

Figure 2:
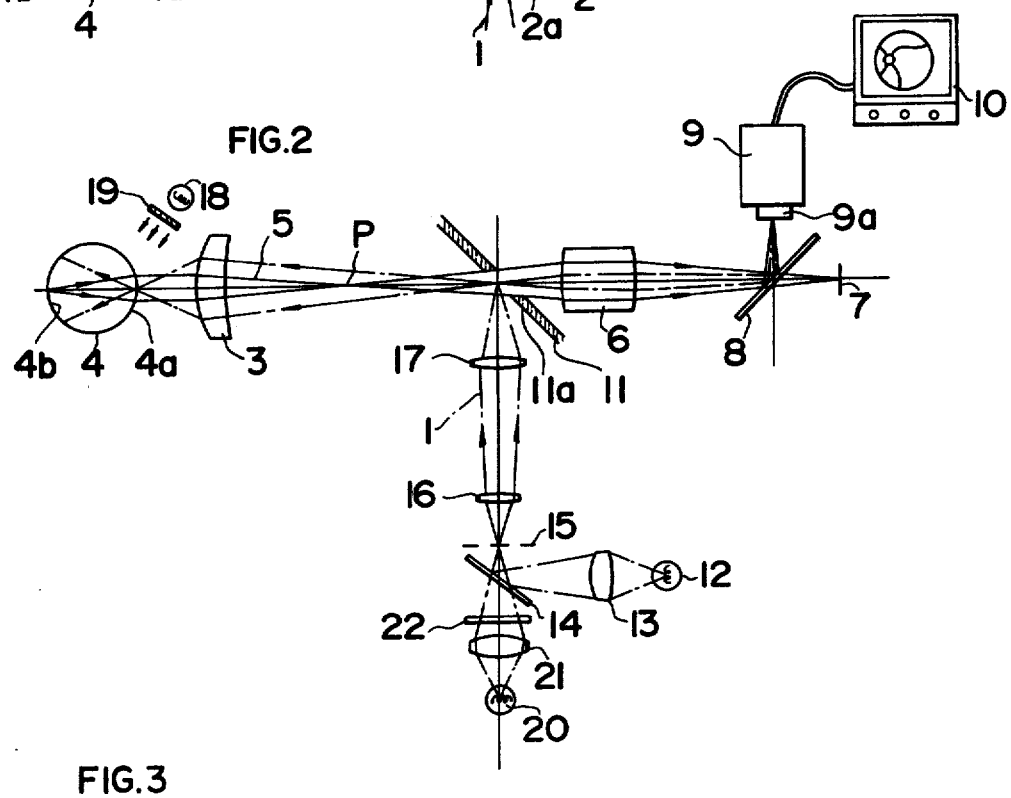
FIG. 2 represents a schematic partial cross-sectional view of an embodiment of the present invention.

The present invention will hereinafter be described in detail. FIG. 2 is a sectional view showing an embodiment of the invention, which has been constructed as a non-mydriasis eye fundus camera. The same reference numerals designate like parts as shown in FIG. 1.

One of the important features of this invention resides in the use of a wavelength-selective apertured filter 11 in lieu of the apertured mirror 2 of the prior art eye fundus camera depicted in FIG. 1. Indicated by the reference numeral 12 is an electronic flash tube to provide a photographing light source, the light output of which is condensed by a condenser lens 13 onto a ring aperture 15 via a half-mirror 14. The image of the ring aperture is focused by lenses 16 and 17 on the apertured filter 11 at the periphery 11a of the aperture. The wavelength selectivity characteristic of the apertured filter 11 used in this embodiment is shown in FIG. 3.

Figure 3:
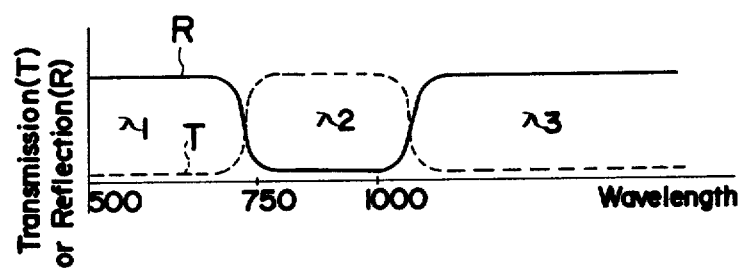
FIG. 3 represents a graphical plot of wavelength transmission of the embodiment of FIG. 2.

Referring to FIG. 3, R stands for reflectance and T stands for transmittance of the filter 11. The photographing light from the electronic flash tube includes light in the visible region indicated by $\lambda_1$ in FIG. 3, the apertured filter 11 selectively reflects light in this wavelength region $\lambda 1$ only toward the objective lens 3 and this light illuminates the eye fundus in the image forming relationship indicated by chain lines 1 just as in FIG. 1. The aperture size of the apertured filter 11 has also been selected just as for the apertured mirror of FIG. 1. The image of the eye fundus 4b illuminated by the photographing light is focused once at point P according to the image forming relationship indicated by the solid line ray trace 5 and further refocused on a film plane 7 by means of relay lens 6 in a similar manner as disclosed in FIG. 1. The light in the wavelength region $\lambda_1$ of the spectrum, as directly reflected from the eye front 4a, returns to the periphery 11a of the aperture as in the case of FIG. 1, but is cut off because, as shown in FIG. 3, the transmittance of the apertured filter 11 to light in the wavelength region $\lambda_1$ is extremely low. Thus, the apertured filter 11 selectively projects only the light of the wavelength region which is able to be reflected toward the eye and, moreover, light in that wavelength region, on return from the eye as it is reflected thereby, cannot pass through the filter area other than the aperture. In this manner, the apertured filter 11 functions in the same manner as the apertured mirror 2 illustrated in FIG. 1 so far as the photographing light is concerned.

The present invention provides a novel monitoring of the front of the eye for alignment purposes as follows. Indicated by reference numeral (18) is an alignment light source which is used to illuminate the eye front (4a) with infrared light at least including rays in the wavelength $\lambda_2$ through an infrared filter 19. The image of the eye front (4a) thus illuminated is focused at the apertured filter which, as illustrated in FIG. 3, has a high transmittance with respect to light in the wavelength region $\lambda_2$ of the spectrum. Thus, with respect to the image of the eye front as formed by light in the wavelength region $\lambda_2$, there exists a situation substantially as if the apertured filter did not exist in the system, with the image over a broad area covering the whole eye front being able to be transmitted toward the relay lens 6. Therefore, the image of the eye front can be easily monitored and the optical system focused by shifting the relay lens 6 in an axial direction until the image of the eye front located at the apertured mirror 11 is refocused on the image-receiving surface 9a of the infrared picture tube 9.

The focusing of the optical system on the eye fundus prior to photographing can be accomplished as follows. The reference numeral 20 signifies a fundus illuminating light source, $\lambda_3$, for focusing, the light output of which is condensed by a condenser lens 21 on the ring aperture 15 through an infrared filter 22 and a half-mirror 14. The infrared filter 22 is capable of transmitting infrared light in a band at least including the wavelength region $\lambda_3$ shown in FIG. 3. The infrared image of the ring aperture 15 is focused by the lenses 16 and 17 on the peripheral area 11a of the aperture filter 11 along the same optical path as that followed by the photographing light from the light source 12. The apertured filter 11 selectively reflects infrared light only in the wavelength region $\lambda_3$ and projects it toward the objective lens. Thereafter, in exactly the same image forming relationship as that of the photographic light, the image of the eye fundus as formed by infrared light in the wavelength region $\lambda_3$ is transmitted to the image-receiving plane 9a of the infrared picture tube 9. It is apparent that not only for the photographing light but also for the fundus-illuminating light, the apertured mirror 11 functions in the same manner as the apertured mirror of FIG. 1. Since the above-described embodiment is directed to a non-mydriasis eye fundus camera, both the front-illuminating light for aligning purposes and the fundus-illuminating light for focusing purposes are infrared beams. Each of the infrared filters 19 and 22, however, need not have characteristics which distinguish between the wavelength regions $\lambda_2$ and $\lambda_3$ it is sufficient that while the infrared filter 19 transmits at least light in the wavelength region $\lambda_2$, the infrared filter 22 transmits at least light in the wavelength $\lambda_3$. It is, therefore, possible to employ infrared filters 19 and 22 of a single kind having a transmission band encompassing both the wavelength regions $\lambda_2$ and $\lambda_3$.

The sequence of operation of this embodiment may be briefly explained, as follows. First, the front of the eye is illuminated by means of the light source 18 and, while monitoring the television screen 10, the relay lens is shifted along the optical axis to focus the image of the eye front on the light receiving plane 9a. Then, while the image of the whole eye front is monitored on the screen 10, the knob of the fundus camera shifting mount, not shown, is operated until the center of the pupil agrees with the intersection of the crossed lines provided on the display screen 10. In this manner, the center line of the pupil is lined up with the photographing optical axis. Then, while the eye fundus is illuminated with the light source 20, the relay lens is shifted along the optical axis to focus the image of the fundus on the image receiving plane 9a as the image on the television screen 10 is monitored. During this operation, the field of view may also be adjusted. In these operations, the pupil is naturally open without any mydriatic eyedrops since the eye is not responsive to the infrared light. Thereafter, the electronic flash tube 12, which is a photographing light source, is actuated to photograph the eye fundus.

While the above embodiment has been designed for use as a non-mydriasis eye fundus camera, the principles of the present invention are, of course, applicable to any ordinary eye fundus camera used in conjunction with mydriatic eyedrops. In such applications, the infrared filters 19 and 22 may be dispensed with and the apertured filter 11 may be such that it has a wavelength selection characteristic which discriminates between the light outputs of the light sources 12 and 20, which are involved in the fundus-illuminating function, and the light output of the light source 18 for illuminating the eye front.

It is apparent from the above description that, in accordance with this invention, when a wavelength selective apertured filter is employed in lieu of the conventional apertured mirror, both the image of the eye fundus without the directly reflected light from the front of the eye which is objectionable for photographing purposes and also the eye image over a broad area of the eye front for alignment purposes is transmitted to the back side of the apertured filter without requiring any lens switching operation. Therefore, the operation of focusing the image of the eye fundus on a film plane for photographing and the operation of focusing the image of the eye front on the focal plane of the monitoring unit for pupil alignment are mere focusing manipulations. In other words, both the aligning of the pupil with the photographing optical axis and the photographing of the eye fundus are made possible by focusing adjustments which may be effected by well-known procedures. By way of illustration of a very simple focussing arrangement, the relay lens can be simply shifted along the optical axis.

Moreover, when this invention is constructed as a non-mydriasis eye fundus camera, in which infrared light is used as the eye-front-illuminating light for aligning the photographing optics with the pupil of the eye and the eye fundus is illuminated with infrared light for focus setting and eye fundus monitoring using the same optical path as that of the photographing light, the aforesaid aligning operation can be easily accomplished, without losing the functions offered by the conventional apertured mirror. By using an apertured filter capable of discriminating between three wavelength regions to keep separate the infrared light for illuminating the eye front, the photographing light in the visible region and the infrared light for illuminating the eye fundus, an improved optical alignment system is provided.

It is to be further understood that various modifications of the generic concepts of this invention are possible without departing from its spirit and accordingly the scope of the present invention should be determined solely from the following claims.

What is claimed is:

1. An improved eye fundus camera for photographing the fundus of an object eye comprising:
    an objective lens capable of optical positioning relative to the object eye and a photographic focal plane;
    a wavelength selective filter for reflecting at least a first wavelength of light in a first band of wavelengths and transmitting at least a second wavelength of light in a second band of wavelengths other than the first band, the filter further being provided with a fully transmissive portion and being positioned relative to the eye and objective lens so that it is substantially conjugate to the front of the object eye with respect to the objective lens;
    a first light source including at least a first wavelength for directing light toward the fundus of the object eye by way of the reflection on the wavelength selective filter, and
    a second light source including at least a second wavelength for directing light towards the front of the object eye, whereby the light of the first light source reflected from the object eye to the wavelength selective filter is transmissible only through the fully transmissive portion thereof, and the light of the second light source reflected from the object eye to the wavelength selective filter is transmissible through any portion thereof.

2. The invention of claim 1, wherein the fully transmissive portion of the wavelength selective filter is an aperture bored therethrough.

3. The invention of claim 1, wherein the first band of wavelengths corresponds to the visible light band, and the second band of wavelengths to an infrared light band.

4. The invention of claim 3, wherein the wavelength selective filter is adapted to reflect substantially all the first band of wavelengths.

5. The invention of claim 1, wherein the wavelength selective filter is further adapted for reflecting at least a third wavelength of light in a third band of wavelengths other than the first and second bands, and the eye fundus camera further comprises a third light source including a third wavelength for directing light toward the fundus of the object eye by way of the reflection on the wavelength selective filter, whereby the light of the third light source reflected from the object eye to the wavelength selective filter is transmissible only through the fully transmissive portion thereof.

6. The invention of claim 5, wherein the first band of wavelengths corresponds to the visible light band, the second band of wavelengths to a first infrared light band, and the third band of wavelengths to a second infrared light band other than the first infrared light band.

7. The invention of claim 6, wherein the wavelength selective filter is adapted to reflect substantially all the first band of wavelengths.

8. The invention of claim 6 further comprising means for directing the light of the first and third light source to the periphery of the fully transmissive portion of the wavelength selective filter so that the light is reflected on the wavelength selective filter toward the fundus of the object eye.

9. The invention of claim 6 further comprising a relay lens positioned between the wavelength selective filter and the focal plane, and means having a light receiving surface positioned to be optically equivalent to the focal plane for monitoring the image on the focal plane, the light receiving surface of the monitoring means being sensitive to at least the second and third wavelengths of light.

10. The invention of claim 9, wherein the relay lens is shiftable along the optical axis for the purpose of focusing.

11. The invention of claim 10, wherein the first light source is an electronic flash tube which is directed to reflect off the wavelength selective filter.

12. The invention of claim 1 further comprising a relay lens positioned between the wavelength selective filter and the first photographic focal plane, and a second focal plane optically equivalent to the first focal plane for monitoring the image on the first focal plane.

13. The invention of claim 12, wherein the relay lens is shiftable along the optical axis for the purpose of focusing.

* * * * *